United States Patent [19]

Mizutani et al.

[11] Patent Number: 4,666,566

[45] Date of Patent: May 19, 1987

[54] METHOD OF DETECTING OXYGEN PARTIAL PRESSURE

[75] Inventors: Yoshihiko Mizutani; Kazuyoshi Shibata, both of Nagoya, Japan

[73] Assignee: NGK Insulators, Ltd., Japan

[21] Appl. No.: 784,040

[22] Filed: Oct. 4, 1985

[30] Foreign Application Priority Data

Oct. 8, 1984 [JP]   Japan .................................. 59-210867

[51] Int. Cl.$^4$ ........................................... G01N 27/58
[52] U.S. Cl. ..................................... 204/1 T; 204/410; 204/412; 204/425
[58] Field of Search ................. 204/1 S, 425, 410, 412

[56] References Cited

U.S. PATENT DOCUMENTS

| | | | |
|---|---|---|---|
| 3,514,377 | 5/1970 | Spacil et al. | 204/1 T |
| 4,158,166 | 6/1979 | Isenberg | 204/1 T X |
| 4,177,112 | 12/1979 | Suzuki et al. | 204/1 T |
| 4,224,113 | 9/1980 | Kimura et al. | 204/1 T |
| 4,272,330 | 6/1981 | Hetrick | 204/1 T |
| 4,272,331 | 6/1981 | Hetrick | 204/1 T |
| 4,356,065 | 10/1982 | Dietz | 204/1 T |
| 4,450,065 | 5/1984 | Yamada et al. | 204/412 |
| 4,498,968 | 2/1985 | Yamada et al. | 204/412 |
| 4,566,419 | 1/1986 | Ninomiya et al. | 123/489 |

FOREIGN PATENT DOCUMENTS

| | | | |
|---|---|---|---|
| 3021745 | 12/1980 | Fed. Rep. of Germany | 204/425 |
| 3226603 | 9/1983 | Fed. Rep. of Germany | 204/425 |

OTHER PUBLICATIONS

IEEE Transactions on Electron Devices, vol. ED-29 (1982) Jan. No. 1, New York "Oscillatory-Mode Oxygen Sensor" by Robert E. Hetrick, W. A. Fate & Wm. C. Vassell.

Primary Examiner—G. L. Kaplan
Attorney, Agent, or Firm—Parkhurst & Oliff

[57] ABSTRACT

A method of effecting determination whether a measurement gas is a rich-burned exhaust gas or a lean-burned exhaust gas, by using an oxygen concentration sensor which includes at least one solid electrolyte member of an oxygen-ion conductive material, and at least two electrodes, one electrode being an electrode which is exposed to the measurement gas through diffusion-resistance means, the steps of: applying an electric current to the electrode exposed to the measurement gas through the diffusion-resistance means, such that the electric current flows in one of opposite directions depending upon whether the measurement gas is a rich-burned exhaust gas or a lean-burned exhaust gas, so as to maintain an atmosphere adjacent to the electrode exposed to the measurement gas through the diffusion-resistance means to be stoichiometric; and detecting one of a change in the direction of flow of the electric current, and a change in polarity of a voltage which gives the electric current, and thereby effecting the determination.

11 Claims, 11 Drawing Figures

METHOD OF DETECTING OXYGEN PARTIAL PRESSURE

BACKGROUND OF THE INVENTION

1. Field of the Art

The present invention relates to a method of determining an oxygen partial pressure of a measurement gas, and more particularly to a method suitable for reliable determination of whether a measurement exhaust gas is a rich-burned exhaust gas or a lean-burned exhaust gas, and for fast and efficient measurement of an oxygen partial pressure of the exhaust gas.

2. Related Art Statement

There have been known various electrochemical devices, each of which comprises an electrochemical cell using a solid electrolyte body. Such electrochemical devices are used, for example, as oxygen sensors to detect the oxygen concentration of an exhaust gas (combustion exhaust gas) produced by internal combustion engines of automotive vehicles. Typical examples of such oxygen sensors include an oxygen sensor which employs a mass of oxygen-ion conductive solid electrolyte such as zirconia ceramics, to determine the oxygen concentration according to the principle of an oxygen concentration cell.

An oxygen sensor (sensor for detecting the oxygen concentration of a gas) as such known type of electrochemical devices is capable of detecting an electromotive force which is induced between a measuring electrode disposed on the solid electrolyte body and exposed to the exhaust gas, and a reference electrode exposed to a reference gas, due to a difference in oxygen concentration between the exhaust gas and the reference gas. By detecting the electromotive force, the oxygen sensor determines whether the measurement gas, i.e., the exhaust gas is a rich-burned exhaust gas or a lean-burned exhaust gas. The rich-burned exhaust gas is produced during combustion of an air-fuel mixture whose air-fuel (A/F) ratio is lower than the stoichiometric air-fuel ratio at which a stoichiometric exhaust gas is produced. The lean-burned exhaust gas is emitted when the air-fuel ratio of the air-fuel mixture is higher than the stoichiometric air-fuel ratio. Thus, the engine which produces the exhaust gases is controlled based on the determination by the oxygen sensor whether the measurement gas is a rich-burned or a lean-burned exhaust gas.

The above-indicated type of oxygen concentration sensor is adapted to sense the oxygen concentration of the exhaust gases by utilizing a variation in the electromotive force induced where the exhaust gases are produced at air-fuel ratios in the neighborhood of the stoichiometric air-fuel ratio (A/F=14.6), namely, by utilizing the so-called "λ curve". Therefore, the application of the known oxygen concentration sensor is limited to those exhaust gases which are emitted where the air-fuel ratio of the air-fuel mixture is around the stochiometric ratio. The above-indicated types of electrochemical sensors were originally developed and designed as oxygen sensors for sensing a measurement gas such as an exhaust gas which is produced as a result of combustion of an air-fuel mixture at the stoichiometric air-fuel ratio. Recently, however, it has been proposed to use such oxygen sensors as so-called "lean A/F" sensors for sensing a lean-burned exhaust gas which is emitted in combustion of a fuel-lean air-fuel mixture, i.e., as a result of combustion with an excessive amount of air. Namely, the "lean A/F" sensor is capable of detecting the oxygen partial pressure of an oxygen-rich exhaust has whose oxygen partial pressure is higher than that of the stoichiometric air-fuel ratio. In recent years, however, there have been proposed oxygen concentration sensors which are provided with diffusion-resistance means in various forms such as a porous layer and a pin hole or aperture, that provides a predetermined diffusion resistance to the molecules of a component in the measurement gas. Such diffusion-resistance means are provided to widen the application range of the measurement gas.

In an oxygen concentration sensor provided with such diffusion-resistance means, a given component such as oxygen in the measurement gas is introduced into the sensor for contact with its measuring electrode, at a relatively low partial pressure of the component. Hence, this type of oxygen sensor is capable of dealing with not only a lean-burned exhaust gas whose oxygen partial pressure is higher than that of the stochiometric A/F ratio, in other words, which is produced in combustion of an air-rich or fuel-lean air-fuel mixture whose A/F ratio is far higher than 14.6, but also a rich-burned exhaust gas whose oxygen partial pressure is lower than that of the stoichiometric A/F ratio and which contains a large amount of unburned components, that is, which is produced in combustion of a fuel-rich air-fuel mixture whose A/F ratio is lower than 14.6.

PROBLEM SOLVED BY THE INVENTION

As described above, the known oxygen sensor controls a partial pressure of a measurement component in the measurement gas by feeding the component to the measuring electrode through suitable diffusion-resistance means. In this known oxygen sensor, too, the determination of whether the exhaust gas is a rich-burned or lean-burned exhaust gas is accomplished by measuring an electromotive force between the measuring electrode exposed to the exhaust gas and a reference electrode exposed to a reference gas, as in the conventional oxygen sensor previously introduced, in the case where the A/F ratio of an air-fuel mixture which produces the exhaust gas is around 14.6, i.e., the stoichiometric A/F ratio.

In the case where the determination of whether the measurement exhaust gas is a rich-burned or a lean-burned exhaust gas is achieved based on a λ-curve of an electromotive force measured between the two electrodes, as indicated above, there is a time lag or delay between an actual change of the measurement gas from a rich-burned gas to a lean-burned gas or vice versa, and a corresponding variation in the measured electromotive force. Stated differently, the electromotive force is not sufficiently responsive to a change in the measurement gas. Thus, the known oxygen sensor suffers a low response to a change of the measurement gas between the rich-burned and lean-burned exhaust gases. The time lag between the actual change in the measurement gas and the delayed variation in the electromotive force is serious particularly when the oxygen sensor has diffusion-resistance means. Described more specifically, a diffusion resistance of the diffusion-resistance means causes a delay between a variation in the oxygen partial pressure of the exhaust gas due to a change from the rich-burned to the lean-burned exhaust gas or vice versa, and a variation in the oxygen partial pressure at the measuring electrode.

Further, such an oxygen sensor adapted to detect an electromotive force induced between two electrodes suffers another problem that hydrocarbon, hydrogen, carbon monoxide, and other components in a rich-burned exhaust gas react with a metallic component of the measuring electrode, and thereby deteriorate the measuring electrode, even causing a flake-off or separation of that electrode if the deterioration is severe. Thus, the durability of the measuring electrode is reduced. This problem of reduced durability of the measuring electrode may not be considerably alleviated if the diffusion-resistance means is provided so as to cover the measuring electrode. That is, the measuring electrode is exposed to the rich-burned exhaust gas which has diffused through the diffusion-resistance means, whereby the measuring electrode is more or less influenced by the components such as hydrocarbons, hydrogen and carbon monoxide in the diffused rich-burned exhaust gas.

SUMMARY OF THE INVENTION

It is accordingly an object of the present invention to solve the aforementioned problems encountered in the prior art. According to the present invention, there is provided a method of effecting determination whether a measurement gas is a rich-burned exhaust gas or a lean-burned exhaust gas, by using an oxygen concentration sensor which includes at least one solid electrolyte member of an oxygen-ion conductive material, and at least two electrodes comprising an electrode which is exposed to the measurement gas through diffusion-resistance means, comprising the steps of: applying an electric current to the electrode exposed to the measurement gas through the diffusion-resistance means, such that the electric current flows in one of opposite directions depending upon whether a measurement gas is a rich-burned exhaust gas or the lean-burned exhaust gas, so as to maintain a stoichiometric atmosphere adjacent to the electrode exposed to the measurement gas through the diffusion-resistance means; and detecting one of a change in the direction of flow of the electric current, and a change in polarity of a voltage which gives the electric current, thereby effecting the determination.

In the method of detecting an oxygen partial pressure according to the present invention as described above, an electric current is applied to the electrode exposed to the measurement gas through the diffusion-resistance means, so as to maintain a stoichiometric atmosphere adjacent to the above-indicated electrode, namely, so as to keep the atmosphere adjacent to this electrode, substantially identical with an exhaust gas which is produced in combustion of an air-fuel mixture of the stoichiometric air/fuel ratio. To determine whether the measurement gas is a rich-burned exhaust gas or a lean-burned exhaust gas, a change in the direction of flow of the electric current or a change in the polarity of a voltage which gives the electric current, is detected. This method of detection is different from the conventional method based on a λ-curve of an electromotive force induced in a sensor. In this arrangement of the invention, the direction of the current flow is reversed when the normally stoichiometric atmosphere adjacent to the above-indicated electrode is changed into a rich-burned exhaust gas or a lean-burned exhaust gas. Therefore, a change of reversal of the direction of flow of the electric current, or a change in the polarity of the voltage takes place in a far shorter time after the change in the measurement gas than a change in the electromotive force beyond a given level due to the change in the measurement gas.

Since the electrode exposed to the measurement gas through the diffusion-resistance means is adapted to be held exposed to a substantially stoichiometric atmosphere, the rich-burned exhaust gas will not have an adverse effect on that electrode, as experienced in the prior art. Stated more specifically, the electrode will not suffer a problem which is conventionally caused due to a reaction of a metallic component of the electrode with unburned components in the rich-burned exhaust gas. Accordingly, the durability of the electrode is increased, and the life expectancy of the oxygen concentration sensor is improved.

According to one embodiment of the invention, the oxygen concentration sensor comprises a solid electrolyte member of an oxygen-ion conductive material, diffusion-resistance means having a predetermined diffusion resistance to the measurement gas, a first electrode disposed between the solid electrolyte member and the diffusion resistance means and exposed to the measurement gas through the diffusion-resistance means, and a second electrode disposed on the solid electrolyte member and exposed to a reference gas, the electric current being applied between the first and second electrode so as to maintain a substantially stoichiometric atmosphere adjacent to the first electrode. The determination whether the measurement gas is the rich-burned or lean-burned exhaust gas may be effected by detecting a change in the direction of flow of the electric current between the first and second electrodes, or a change in the polarity of the voltage.

According to one form of the above embodiment, ambient air is used as the reference gas. In this instance, an electromotive force induced between the first and second electrodes by means of an electrochemical reaction is generally varied between 0V and about 1V as the measurement gas changes from a lean-burned exhaust gas into a rich-burned exhaust gas. Accordingly, it is desired in this case that the electric current is applied between the first and second electrodes so that a potential difference between the first and second electrodes is held within a range of 0.2–0.7 V, preferably within a range of 0.3–0.6 V.

According to another embodiment of the invention, the oxygen concentration sensor comprises: (a) diffusion-resistance means having a predetermined diffusion resistance to the measurement gas; (b) a pumping cell which includes a first solid electrolyte member of an oxygen-ion conductive material, an outer or a first pumping electrode disposed on the first solid electrolyte member and exposed, for example, to the measurement gas, and an inner or a second pumping electrode disposed on the first solid electrolyte member and exposed, for example, to the measurement gas through the diffusion-resistance means; and (c) a sensing cell which includes a second solid electrolyte member, a reference electrode disposed on the second solid electrolyte member and exposed to a reference gas, and a measuring electrode disposed on the second solid electrolyte member and exposed to an atmosphere which is substantially the same as an atmosphere to which the inner pumping electrode is exposed. In this case, the electric current is applied between the outer and inner pumping electrodes of the pumping cell, according to an electromotive force induced between the reference and measuring electrodes of the sensing cell, so as to maintain a stoichiometric atmosphere to which the inner pumping electrode is exposed. The determination of whether the measurement gas is a rich- or lean-burned exhaust gas is accomplished by detecting a change in the direction of flow of the electric current between the outer and inner pumping electrode, or a change in the polarity of the voltage.

In the above embodiment, ambient air is used as the reference gas to which the reference electrode of the sensing cell is exposed. In this instance, too, the electric current is applied in an appropriate direction between the outer and inner pumping electrodes of the pumping cell, so that a potential between the measuring and reference electrodes of the sensing cell is held within a range of 0.2–0.7 V, preferably 0.3–0.6 V, in order to maintain a substantially stoichiometric atmosphere to which the measuring electrode and the inner pumping electrode are exposed.

According to an advantageous embodiment of the invention, the diffusion-resistance means consists of a porous ceramic layer having a predetermined diffusion resistance. When the oxygen sensor includes both pumping and sensing cells, the first solid electrolyte member of the pumping cell may be formed as a porous layer which serves as a diffusion-resistance means. It is possible that a diffusion-resistance means is constituted by a pin hole or aperture or a slit which has the predetermined diffusion resistance. In this case, the appropriate electrode is exposed to the measurement gas through the aperture or slit.

BRIEF DESCRIPTION OF THE DRAWINGS

The above and other objects, features and advantages of the present invention will be better understood from the following detailed description of preferred embodiments of the invention, when taken in connection with the accompanying drawings, in which.

DETAILED DESCRIPTION OF THE PREFERRED EMBODIMENTS

To further illustrate the concept of the present invention, several preferred embodiments thereof will be described in detail with reference to the accompanying drawing.

Figure 1A:
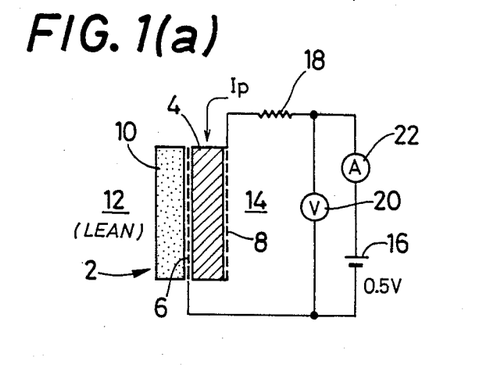
FIGS. 1(a) and 1(b) are schematic views showing one embodiment of this invention, wherein a sensor is exposed to a lean-burned exhaust gas in FIG. 1(a), while the sensor is exposed to a rich-burned exhaust gas in FIG. 1(b)
Figure 1B:
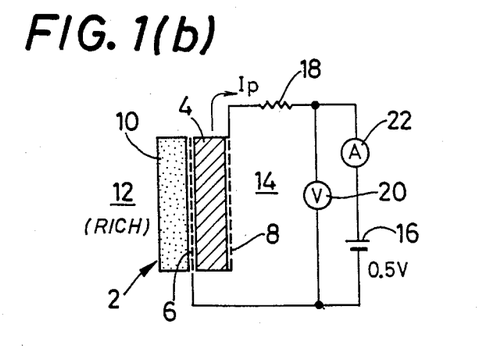

Referring first to FIGS. 1(a) and 1(b), there is shown an example of one of the most basic types of arrangements of an electrochemical system for detecting an oxygen partial pressure of a measurement gas. In the figures, reference numeral 2 generally and schematically indicates a detecting portion of a sensing element of an oxygen sensor. The detecting portion 2 consists of: a solid electrolyte layer 4 made of an oxygen-ion conductive ceramic material such as zirconia ceramics containing yttria; a first and a second porous electrode 6, 8 made of platinum for example, which are disposed on opposite surfaces of the solid electrolyte layer 4; and a porous ceramic layer 10 made of alumina or another ceramic material, which is formed on the surface of the solid electrolyte layer 4 carrying the first electrode 6, so as to cover the first electrode 6. The sensing element is positioned so that the porous ceramic layer 10 of the oxygen detecting portion 2 is exposed to a measurement gas 12 to be detected by the sensing element. The measurement gas diffuses through the porous ceramic layer 10, with a predetermined diffusion resistance, and is directed toward the solid electrolyte layer 4 so that the measurement gas 12 contacts the first electrode 6 positioned between the porous ceramic layer 10 and the solid electrolyte layer 4. Also, the sensing element is adapted to expose the second electrode 8 to a suitably introduced reference gas 14, usually ambient air, which has a given oxygen concentration.

The solid electrolyte layer 4 of the oxygen sensing element of the aforementioned construction, which is preferably made of zirconia ceramics described, may be made of suitable oxygen-ion conductive materials such as $SrCeO_3$, or a solid solution of a $Bi_2O_3$-oxide of a rare earth element. On the other hand, the first and second electrodes 6, 8 formed on the surfaces of the solid electrolyte layer 4 are porous layers which may be formed from a mixture which consists of an element selected from the platinum group comprising platinum, palladium, rhodium, iridium, ruthenium and osmium, and an element selected from the ceramic group including zirconia, yttria and alumina. According to a preferred process of forming the porous layers of the electrodes of such a mixture, a metal powder mass of the platinum group is mixed with a ceramic powder mass of the ceramic group, and the obtained mixture powder mass is used to form layers which are fired into the porous layers of the electrodes. While the porous ceramic layer 10 is preferably formed of porous alumina, it may be made of other ceramics such as spinel, silica, zirconia, and zircon, titanate of alkaline earth metal.

For detecting the measurement gas in the form of a combustion exhaust gas in the present oxygen concentration sensing element of the foregoing construction, the first and second electrodes 6, 8 are connected through their leads to an external power source 16, so that a predetermined reference voltage is applied between these electrodes 6, 8. In other words, the power source 16 applies the predetermined reference voltage (0.5 V in this example) between the first and second electrodes 6, 8 so that the atmosphere around or in the vicinity of the first electrode 6 is maintained to be stoichiometric or almost stoichiometric. In FIGS. 1(a) and 1(b), reference numerals 18 and 20 designate a resistor and a voltmeter, respectively, while reference numeral 22 indicates an ammeter for detecting a direction in which an electric current flows in the circuit.

The detection of the measurement gas by the sensing element (2) is effected with the reference voltage (potential difference) of 0.5 V applied between the first and second electrodes 6, 8 so as to keep the first electrode 6 exposed to a stoichiometric or almost stoichiometric atmosphere. Stated in greater detail, the measurement gas 12 diffuses toward the solid electrolyte layer 4 through the porous ceramic layer 10 with a predetermined diffusion resistance, and reaches the first electrode 6, thereby causing the atmosphere adjacent to the first electrode 6 to be changed to conform with the measurement gas 12, i.e., a lean-burned exhaust gas or a rich-burned exhaust gas depending upon the kind of the measurement gas 12 which has reached the first electrode 6. A change in the atmosphere adjacent to the first electrode 6 will cause a difference (unbalance) between an electromotive force induced between the first and second electrodes 6, 8 according to the principle of an oxygen concentration cell (electrochemical reaction), and the reference voltage (0.5 V) applied by the power source 16. As a result, according to a magnitude of the electromotive force between the two electrodes 6, 8, an electric current flows in one of opposite directions in a circuit including the electrodes 6, 8 and the power source 16.

However, when the measurement gas 12 is a stoichiometric atmosphere identical with the atmosphere adjacent to the first electrode 6, that is, when the measurement gas 12 has an oxygen partial pressure which is equivalent to that of an exhaust gas which is produced in combustion of an air-fuel mixture of the stoichiometric A/F ratio, the oxygen partial pressure of the atmosphere adjacent to the first electrode 6 will not be affected by the measurement gas 12. Therefore, the electromotive force induced between the first and second electrodes 6, 8 is equal to the reference voltage applied by the power source 16. In this case, an electric current will not flow in the circuit including the electrodes 6, 8 and the power source 16.

Described in more detail referring to FIG. 1(a), an electric current Ip flows in the circuit where the measurement gas 12 is a lean-burned exhaust gas which is produced during combustion of an air-fuel mixture of an A/F ratio greater than 14.6 and which has a high oxygen partial pressure. In this case, oxygen in the lean-burned exhaust gas 12 diffuses through the porous ceramic layer 10 and reaches the first electrode 6, thereby raising the oxygen partial pressure of the atmosphere adjacent to the first electrode 6. Hence, the electromotive force generated between the first and second electrodes 6, 8 on the opposite sides of the solid electrolyte layer 4 is reduced below 0.5 V, whereby an electric current Ip flows from the second electrode 8 to the first electrode 6. Accordingly, the oxygen adjacent to the first electrode 6 is moved as oxygen ions through the solid electrolyte layer 4 to the second electrode 8, and discharged in the reference gas 14. The electric current Ip continues to flow from the second electrode 8 to the first electrode 6 until the atmosphere adjacent to the first electrode 6 becomes an atmosphere which is given by the reference voltage of 0.5 V of the power source 16, in other words, until the oxygen partial pressure of the atmosphere adjacent to the first electrode 6 becomes equal to the oxygen partial pressure of the atmosphere given by the power source 16. During the flow of the electric current Ip, the oxygen in the atmosphere adjacent to the first electrode 6 is pumped into the reference gas 14.

In the case where the measurement gas 12 is a rich-burned exhaust gas which is produced in combination of an air-fuel mixture of an A/F ratio below 14.6 and which has a low oxygen partial pressure, an electric current Ip flows in the reverse direction as shown in FIG. 1(b), i.e., in the direction opposite to that in FIG. 1(a). In this case, unburned components in the rich-burned exhaust gas which has diffused through the porous ceramic layer 10 and reached the first electrode 6, react with the oxygen in the stoichiometric atmosphere existing adjacent to the first electrode 6, whereby the oxygen concentration (oxygen partial pressure) of the atmosphere adjacent to the first electrode 6 is reduced. As a result, an electromotive force generated by an electrochemical reaction between the first and second electrodes 6, 8 on the opposite surfaces of the solid electrolyte layer 4 exceeds the reference voltage of 0.5 V of the power source 16. Consequently, the electric current Ip flows in the circuit including the electrodes 6, 8 and power source 16, in a clockwise direction as viewed in FIG. 1(b), i.e., from the first electrode 6 to the second electrode 8. With this clockwise flow of the current Ip, the oxygen in the reference gas 14 is moved toward the first electrode 6 through the solid electrolyte layer 4, whereby the atmosphere adjacent to the first electrode 6 is made stoichiometric (into an atmosphere corresponding to the reference voltage of 0.5 V of the power source 16). In other words, the flow of the electric current Ip continues until the atmosphere adjacent to the first electrode 6 has been neutralized.

As described above, with the predetermined reference voltage (0.5 V) applied between the first and second electrodes 6, 8, an electric current Ip flows therebetween so as to keep the atmosphere adjacent to the first electrode 6 stoichiometric or almost stoichiometric. Since the direction of flow of the electric current Ip in the circuit including the electrodes 6, 8 is determined by the kind of the measurement gas 12, that is, reversed when the measurement gas 12 is changed between a rich-burned and a lean-burned exhaust gas, it is possible to easily determine whether the measurement gas 12 is a rich-burned exhaust gas or a lean-burned exhaust gas.

Figure 2A:
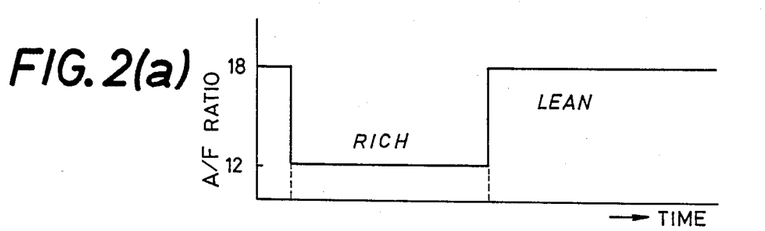
FIGS. 2(a), 2(b) and 2(c) are graphs showing respectively, a change in the measurement gas, a variation in pump current of the sensor of FIGS. 1(a) and 1(b), and a variation in electromotive force of the same sensor.
Figure 2B:
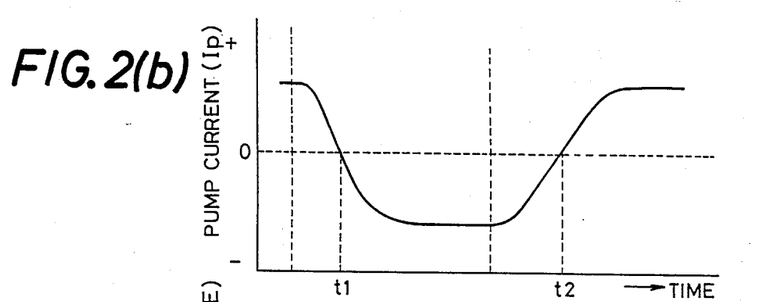
Figure 2C:
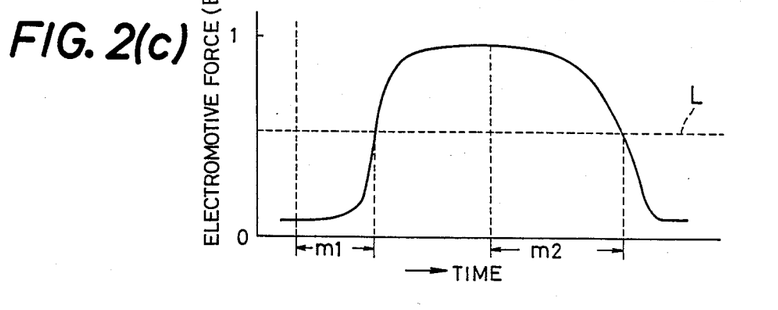

According to the present method as described hitherto, a change of the measurement gas from a rich-burned exhaust gas to a lean-burned exhaust gas or vice versa is sensed by detecting a change in the direction of flow of the electric current Ip (i.e., pump current) between the first and second electrodes 6, 8 so as to maintain a stoichiometric atmosphere adjacent to the first electrode 6. As indicated in FIGS. 2(a)-2(c), a time lag between a change in the measurement gas and a change in the direction of flow of the pump current Ip is far smaller than a time lag between the change in the measurement gas and a change in an electromotive force indicating the change in the measurement gas. (The response of the pump current Ip to the change in the mesurement gas 12 is about two times as high as that of the electromotive force.) Described in greater detail, FIG. 2(a) indicates changes in the measurement gas 12 between a rich-burned exhaust gas produced in combustion of an air-fuel mixture of an A/F ratio of 12, and a lean-burned exhaust gas produced in combustion of an air-fuel mixture of an A/F ratio of 18. A variation in the pump current Ip corresponding to the changes in the measurement gas 12 is shown in FIG. 2(b), while a variation in the electromotive force E is shown in FIG. 2(c). It will be apparent, from the graphs in these figures, that points of time t1 and t2 at which the direction of flow of the pump current Ip is changed, take place a relatively short time after the moments when the measurement gas 12 is changed from a lean-burned exhaust gas to a rich-burned exhaust gas, or vice versa.

The changes in the electromotive force E of FIG. 2(c) that correspond to the changes in the measurement gas, occur only after the atmosphere adjacent to the first electrode 6 has been completely changed from a rich-burned exhaust gas to a lean-burned exhaust gas or vice versa. Therefore, there should be a considerably long period of time m1 or m2 between the change in the measurement gas and a point of time at which a curve of the electromotive force E crosses a reference line L which corresponds to the moment of the change in the measurement gas. Namely, the determination whether the measurement gas is a rich-burned or a lean-burned exhaust gas is accordingly delayed. In this connection, it is noted that the diffusion resistance of the porous ceramic layer 10 through which the measurement gas diffuses toward the first electrode 6 causes a delay between the change in the measurement gas 12 and the change in the atmosphere adjacent to the first electrode 6.

According to the method of the present invention, on the contrary, the pump current Ip flows so as to maintain the stoichiometric or almost stoichiometric atmosphere adjacent to the first electrode 6. Therefore, the change in the atmosphere adjacent to the first electrode 6 from the stoichiometric atmosphere to a rich-burned or a lean-burned atmosphere can be detected in a comparatively short time after the change in the measurement gas 12, by detecting a change (reversal) of the direction of flow of the pump current Ip which flows in a direction to keep the atmosphere adjacent to the first electrode 6 stoichiometric. In other words, a comparatively short time is required to detect the point of time t1 or t2 at which the flow direction of the pump current Ip is changed.

As described above, the method of the present invention permits a fast detection of a change in the measurement gas between the rich-burned and lean-burned exhaust gases, by sensing a change in the flow direction of the pump current Ip. Thus, it is possible to efficiently and effectively regulate the measurement gas, for example, exhaust gases of an internal combustion engine of an automotive vehicle, so that the exhaust gases are made stoichiometric, namely, so that the combustion condition of the engine is suitably controlled.

Since the atmosphere adjacent to the first electrode 6 is controlled so as to maintain stoichiometric or almost stoichiometric according to the present method, the rich-burned exhaust gas which has diffused through the porous ceramic layer 10 to the first electrode 6 is diluted by the oxygen which is transferred from the reference gas 14. Consequently, the first electrode 6 is protected against deterioration due to the reaction with the rich-burned exhaust gas, and against a consequent decline in its durability.

Figure 3:
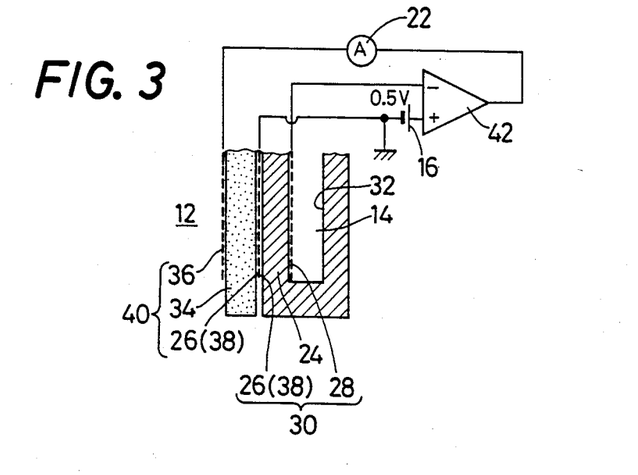
FIGS. 3, 4 and 6 are schematic views showing further embodiments of the invention.
Figure 4:
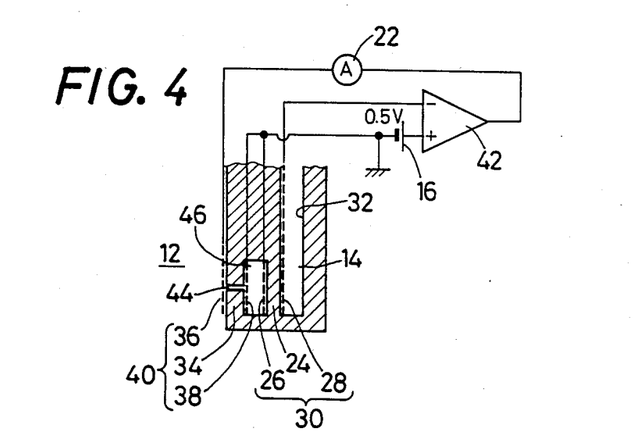

While the method of the invention has been described in connection with the sensing element of the oxygen concentration sensor as illustrated in FIGS. 1(a) and 1(b), the present method may be practiced on oxygen concentration sensors, as shown in FIGS. 3 and 4. These sensors have a sensing element which includes an electrochemical pumping cell capable of effecting an oxygen pumping operation, and an electrochemical sensing cell for detecting an electromotive force. In this case, it is possible to eliminate a problem of an IR drop of the sensing cell due to an influence by a pump current of the pumping cell, and thereby enhance the detecting accuracy of the sensor.

In an arrangement of FIG. 3, a sensing cell 30 is constituted by a solid electrolyte layer 24 of an oxygen-ion conductive material, and a measuring and a reference electrode 26, 28 of a porous structure which are disposed on opposite surfaces of the solid electrolyte layer 24. In this sensing cell 30, an electromotive force is induced between the measuring and reference electrodes 26, 28 according to the principle of an oxygen concentration cell. In the sensing element, an air-passage 32 is formed, so that the reference electrode 28 of the sensing cell 30 is exposed to ambient air which is introduced into the air-passage 32 as a reference gas.

On the surface of the sensing cell 30 on which the measuring electrode 26 is disposed, there is formed a pumping cell 40 which cooperates with the sensing cell 30 to form an integral laminar structure. The pumping cell 40 includes a porous solid electrolyte layer 34 of an oxygen-ion conductive material, an outer pumping electrode 36 which is disposed on an outer exposed surface of the porous solid electrolyte layer 34, and an inner pumping electrode 38 on an inner surface of the solid electrolyte layer 34. The inner pumping electrode 38 and the measuring electrode 26 are constituted by a single common electrode. The sensing element is located so that the outer pumping electrode 36 of the pumping cell 40 is exposed to a measurement gas 12. The measurement gas 12 diffuses through the porous solid electrolyte layer 34 with a predetermined diffusion resistance, and reaches the inner pumping electrode 38. In the present embodiment, the porous solid electrolyte layer 34 itself functions as diffusion-resistance means like the porous ceramic layer 10 of FIGS. 1(a) and 1(b).

The measuring electrode 26 and the reference electrode 28 of the sensing cell 30 are connected to a power source 16 as used in the preceding embodiment, so that a predetermined reference voltage (0.5 V) is applied between the measuring and reference electrodes 26, 28. The potential difference of 0.5 V given by the power source 16, and an electromotive force induced in the sensing cell 30 are applied to respective inputs of a differential amplifier 42, so that the amplifier 42 provides an output of a positive or negative current proportional to a difference between the potential difference and the electromotive force, in order that an atmosphere adjacent to the measuring electrode 26 is maintained to be stoichiometric or almost stoichiometric. This output current from the differential amplifier 42 flows between the outer and inner pumping electrodes 36, 38 of the pumping cell 40, whereby oxygen ions move from the outer pumping electrode 36 toward the inner pumping electrode 38, or vice versa. Thus, the pumping cell 40 performs an oxygen pumping operation. An ammeter 22 is provided to detect the direction of flow of the electric current induced by the differential amplifier 42. The single common electrode serving as the measuring electrode 26 of the sensing cell 30 and the inner pumping electrode 38 of the pumping cell 40 is grounded.

In the arrangement of the present oxygen concentration sensor using the independent sensing and pumping cells 30, 40, the electromotive force of the sensing cell 30 is detected to maintain the atmosphere adjacent to the measuring electrode 26 (inner pumping electrode 38) to be stoichiometric or almost stoichiometric, and a suitable amount of electric current is induced based on the detected electromotive force. Therefore, when the atmosphere adjacent to the measuring electrode 26 is changed due to a measurement component of the measurement gas which has diffused through the porous solid electrolyte layer 34 of the pumping cell 40, the differential amplifier 42 applies the electric current between the outer and inner pumping electrodes 36, 38 of the pumping cell 40 so as to maintain the atmosphere adjacent to the measuring electrode 26 to be stoichiometric, that is, to restore the stoichiometric atmosphere corresponding to the reference voltage of 0.5 V.

When the measurement gas 12 is a rich-burned exhaust gas, a negative current is induced by the differential amplifier 42, whereby the current flows from the inner pumping electrode 38 toward the outer pumping electrode 36 and the oxygen component in the measurement gas moves through the porous solid electrolyte layer 34 toward the inner pumping electrode 38 under an electrochemical reaction. As a result, the oxygen concentration (partial pressure) of the atmosphere adjacent to the inner pumping electrode 38, i.e., measuring electrode 26 is increased, as in the preceding embodiment. If the measurement gas 12 is a lean-burned exhaust gas, on the other hand, the oxygen partial pressure of the atmosphere adjacent to the measuring electrode 26 is increased by the oxygen component which has diffused to the measuring electrode 26 through the porous solid electrolyte layer 34. As a result, the differential amplifier 42 provides a positive current which flows from the outer pumping electrode 36 toward the inner pumping electrode 38, whereby the oxygen in the atmosphere adjacent to the measuring electrode 26 is pumped out into the measurement gas through the porous solid electrolyte layer 34.

Figure 5A:
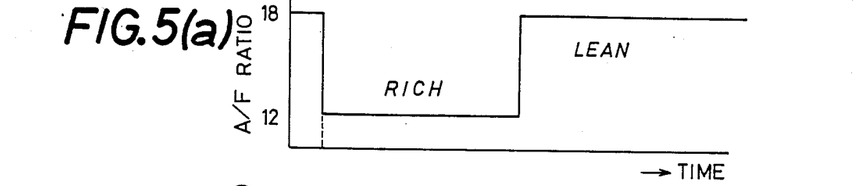
FIGS. 5(a), 5(b) and 5(c) are graphs showing respectively, a change in the measurement gas, a variation in pump current of a sensor of FIG. 3, and a variation in pump voltage of the same sensor.
Figure 5B:
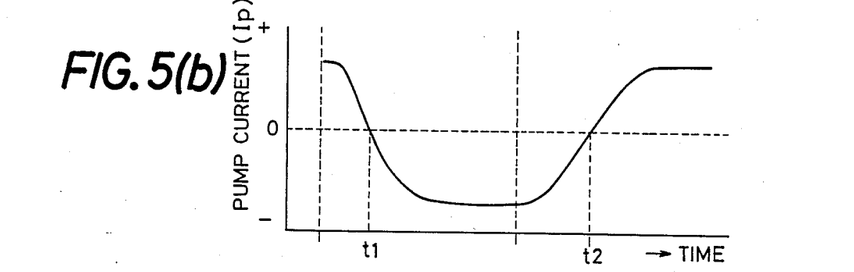
Figure 5C:
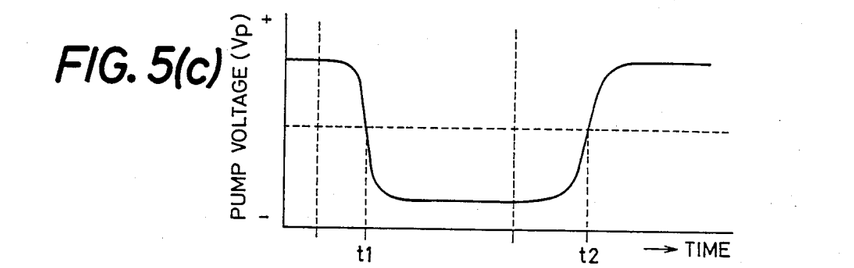

While the above method is arranged to detect change of the direction of flow of the pump current to determine whether the measurement gas is a rich-burned or a lean-burned exhaust gas, it is possible to detect a change of the pump voltage between the outer and inner pumping electrodes 36, 38. Since the pump voltage Vp is varied more abruptly or suddenly than the pump current Ip, as shown in FIG. 5, the determination of the measurement gas by detecting the polarity of the pump voltage Vp is desirable for improving the sensor characteristics.

A further modified sensing arrangement shown in FIG. 4 is slightly different from the oxygen sensing arrangement of FIG. 3. That is, the present arrangement of FIG. 4 is characterized by the use of a pin hole or aperture 44 as diffusion-resistance means. More specifically, the sensing element of the present oxygen concentration sesor has a cavity 46 surrounded by the sensing and pumping cells 30, 40. The aperture 44 has a diameter selected to provide a predetermined diffusion resistance, and is formed through the pumping cell 40, so as to communicate the cavity 46 with the external measurement gas space. Since the aperture 44 is provided as a diffusion-resistance means, the solid electrolyte layer 34 of the pumping cell 40 is formed as a gas-tight layer, contrary to the porous solid electrolyte layer of the preceding embodiments. Further, the measuring electrode 26 of the sensing cell 30 and the inner pumping electrode 38 of the pumping cell 40 are separate electrodes which are disposed on opposite sides of the cavity 46 and exposed to substantially the same atmosphere in the cavity 46.

In the oxygen concentration sensor of FIG. 4, the measurement gas 12 enters the cavity 46 through the aperture 44 with the predetermined diffusion resistance, and consequently the atmosphere in the cavity 46, that is, the atmosphere contacting the measuring electrode 26 of the sensing cell 30 is changed. As in the preceding arrangement of FIG. 3, the thus changed atmosphere is restored into a stoichiometric or substantially stoichiometric atmosphere by means of an oxygen pumping operation of the pumping cell 40. Since the operations of the sensing and pumping cells 30, 40 in the present arrangement of FIG. 4 are similar to those of the preceding arrangement of FIG. 3, repeated description thereof will be omitted in the interest of brevity.

Figure 6:
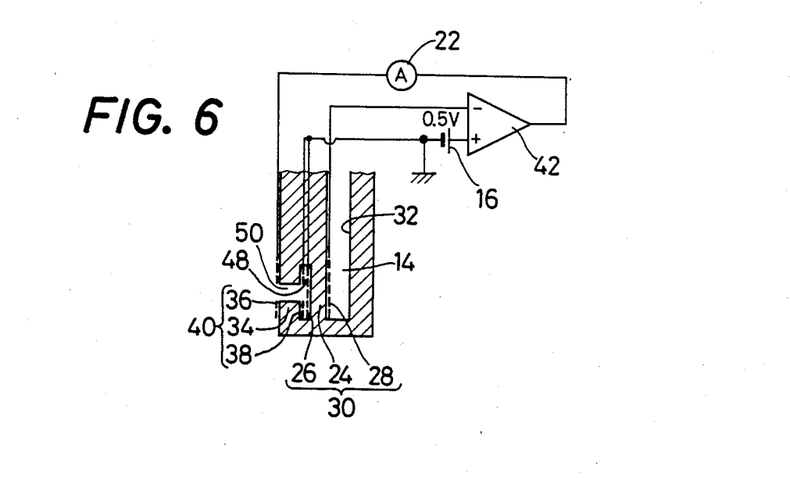

A further modified embodiment of the invention is illustrated in FIG. 6 which is different from the embodiment of FIG. 4, in that the diffusion-resistance means is constituted by a slit 48. Stated in greater detail, the slit 48 is a thin flat space which is disposed between the defined by the sensing and pumping cells 30, 40. The slit 48 communicates with the outside measurement gas through a gas-inlet hole 50 which provides substantially no diffusion resistance to the measurement gas. The measuring electrode 26 of the sensing cell 30 and the inner pumping electrode 38 of the pumping cell 40 are disposed so as to be exposed to the thin flat space of the slit 48. The present oxygen concentration sensor is operated in the same manner as the embodiments of FIGS. 3 and 4, in order to maintain the atmosphere in the slit 48 to be stoichiometric, more precisely, the atmosphere in the inner part of the slit 48 remote from the gas-inlet hole 50. Although the measuring electrode 26 is provided over the entire area of the slit 48, it is desired that the measuring electrode 26 be provided at the inner part of the thin flat space 48 remote from the gas-inlet hole 50.

While the present invention has been described in detail in its several preferred embodiments, it is to be understood that the invention is not confined to the illustrated details, and it will be obvious that the invention may be embodied with various changes, modifications and improvements.

It will be noted that the method of the present invention may be practiced on various arrangements of an oxygen concentration sensor other than those illustrated in the drawing, provided the sensing arrangements use a suitable diffusion-resistance means which has a predetermined diffusion resistance to the measurement gas.

According to the various arrangements of the present invention which have been described, an electric current flows in a direction so as to maintain the atmosphere adjacent to an electrode exposed to the measurement gas which has diffused through suitable diffusion-resistance means to be stoichiometric. The direction of flow of the electric current is changed when the measurement gas is changed from a rich-burned exhaust gas to a lean-burned exhaust gas or vice versa. Therefore, the measurement gas may be sensed by detecting a change of the direction of flow of the electric current. This detecting method permits a significantly improved response of the sensor, as compared with the conventional method in which the measurement gas is detected based on an electromotive force induced between the electrodes. The present method of the invention is suitable for checking combustion exhaust gases produced by internal combustion engines, and is effective for protecting the electrode against deterioration and improving the service life of the sensor. These are industrially significant advantages of the present invention.

What is claimed is:

1. A method of determining whether a measurement gas is a rich-burned exhaust gas or a lean-burned exhaust gas, by using an oxygen concentration sensor which includes at least one oxygen-ion conductive solid electrolyte member, and at least two electrodes, a first of said at least two electrodes being exposed to the measurement gas through diffusion-resistance means, comprising the steps of:

applying an electric current between said first electrode exposed to the measurement gas and a second electrode of said at least two electrodes, such that the electric current flows in one of two opposite directions depending upon whether the measurement gas is a rich-burned exhaust gas or a lean-burned exhaust gas, thereby maintaining an atmosphere adjacent to said first electrode to have a substantially stoichiometric air to fuel ratio and protecting said first electrode from deterioration due to prolonged exposure to said rich-burned exhaust gas; and detecting either a change in a flow direction of said electric current needed to maintain said substantially stoichiometric air to fuel ratio, or a change in polarity of a voltage which supplies the electric current, thereby determining whether said measurement gas is rich-burned or lean-burned depending upon said flow direction or said change in polarity.

2. The method according to claim 1, wherein said oxygen concentration sensor comprises an oxygen-ion conductive solid electrolyte material, diffusion-resistance means having a predetermined diffusion resistance to the measurement gas, said first electrode being disposed between said solid electrolyte material and said diffusion resistance means and being exposed to the measurement gas through said diffusion-resistance mans, and said second electrode being disposed on said solid electrolyte member and exposed to a reference gas.

3. The method of claim 2, wherein said reference gas is ambient air, the electric current being applied between said first and second electrodes while a potential difference between said first and second electrodes is maintained within a range of 0.2–0.7 V.

4. The method of claim 3, wherein said potential difference between said first and second electrodes is maintained within a range of 0.3–0.6 V.

5. The method according to claim 1, wherein said oxygen concentration sensor comprises:

diffusion-resistance means having a predetermined diffusion resistance to the measurement gas;

a pumping cell which includes a first solid electrolyte member of an oxygen-ion conductive material, a first pumping electrode disposed on said first solid electrolyte member and exposed to the measurement gas, and a second pumping electrode disposed on said first solid electrolyte member and exposed to the measurement gas through said diffusion-resistance means;

a sensing cell which includes a second solid electrolyte member, said first electrode of said at least two electrodes being a measuring electrode disposed on said second solid electrolyte member and exposed to said measurement gas, and said second electrode of said at least two electrodes being a reference electrode disposed on said second solid electrolyte member and exposed to a reference gas, said measuring electrode being exposed to an atmosphere which is substantially the same as an atmosphere to which said second pumping electrode is exposed, the electric current being applied between said first and second pumping electrodes of the pumping cell, according to an electromotive force induced between said reference and measuring electrodes of the sensing cell, so as to neutralize the atmosphere to which said second pumping electrode is exposed.

6. The method of claim 5, wherein a single common electrode functions as said second pumping electrode of the pumping cell and said measuring electrode of the sensing cell.

7. The method of claim 5, wherein said first solid electrolyte member of the pumping cell is a porous layer having said predetermined diffusion resistance, and functions as said diffusion-resistance means.

8. The method of claim 5, wherein said reference gas is ambient air, the electric current being applied between said first and second pumping electrodes of the pumping cell while a potential difference between said measuring and reference electrodes of the sensing cell is maintained within a range of 0.2–0.7 V.

9. The method of claim 8, wherein said potential difference between said measuring and reference electrodes of the sensing cell is maintained within a range of 0.3–0.6 V.

10. The method of claim 1, wherein said diffusion-resistance means comprises a porous ceramic layer having said predetermined diffusion resistance.

11. The method of claim 1, wherein said diffusion-resistance means comprises a structural feature selected from the group consisting of an aperture and a slit which has said predetermined diffusion resistance.

* * * * *